United States Patent [19]
Bachynsky

[11] Patent Number: 5,971,953
[45] Date of Patent: Oct. 26, 1999

[54] DUAL CHAMBER SYRINGE APPARATUS

[76] Inventor: Nicholas Bachynsky, 701 W. 14th St., Texarkana, Tex. 75501

[21] Appl. No.: 09/005,221

[22] Filed: Jan. 9, 1998

[51] Int. Cl.⁶ .................................................. A61M 37/00
[52] U.S. Cl. .............................. 604/90; 604/89; 604/181; 604/187; 604/191
[58] Field of Search .................................. 604/89, 88, 90, 604/91, 92, 181, 184, 187, 191

[56] References Cited

U.S. PATENT DOCUMENTS

| | | | |
|---|---|---|---|
| 2,549,417 | 4/1951 | Brown | 128/272 |
| 2,591,046 | 4/1952 | Brown | 128/218 |
| 4,202,314 | 5/1980 | Smirnov et al. | 128/218 F |
| 4,214,584 | 7/1980 | Smirnov et al. | 128/218 M |
| 4,226,236 | 10/1980 | Genese | 128/218 M |
| 4,312,343 | 1/1982 | Leveen et al. | 128/218 C |
| 4,413,991 | 11/1983 | Schmitz et al. | 604/191 |
| 4,529,403 | 7/1985 | Kamstra | 604/136 |
| 4,583,974 | 4/1986 | Kokernak | 604/211 |
| 4,613,326 | 9/1986 | Szwarc | 604/89 |
| 4,792,329 | 12/1988 | Schreuder | 604/90 |
| 4,874,381 | 10/1989 | Vetter | 604/191 |
| 4,898,580 | 2/1990 | Crowley | 604/90 |
| 4,968,299 | 11/1990 | Ahlstrand et al. | 604/90 |
| 4,978,339 | 12/1990 | Labouze et al. | 604/110 |
| 4,983,164 | 1/1991 | Hook et al. | 604/87 |
| 4,994,043 | 2/1991 | Ysebaert | 604/191 |
| 5,041,088 | 8/1991 | Ritson et al. | 604/88 |
| 5,080,649 | 1/1992 | Vetter | 604/91 |
| 5,267,963 | 12/1993 | Bachynsky | 604/134 |
| 5,273,544 | 12/1993 | Van Der Wal | 604/134 |
| 5,395,326 | 3/1995 | Haber et al. | 604/90 |
| 5,423,752 | 6/1995 | Haber et al. | 604/86 |

FOREIGN PATENT DOCUMENTS 0072057  2/1983  European Pat. Off. .......... A61M 5/20

OTHER PUBLICATIONS

Hamilton, James G., *The Journal of Family Practice*, vol. 41, No. 2 (Aug.) 1995, pp. 169–175.

Ippolito, Giuseppe et al., *JAMA*, Aug. 24/31, 1994, vol. 272, No. 8, pp. 607–610.

Tereskerz, Patricia M. et al., *The New England Journal of Medicine*, "Occupational Exposure To Blood Among Medical Students", Oct. 10, 1996, vol. 335, No. 15., pp. 1150–1153.

Genotropin™ Brochure, Pharmacia & Upjohn, Inc., 1996, 9 pages.

CARDIZEM® Lyo–Ject™ Brochure, 4 pgs. (No. 1.).

The CARDIZEM® (diltiazem HCl) Lyo–Ject™ Delivery System Brochure, 6 pgs.

*Primary Examiner*—Ronald Stright
*Assistant Examiner*—Kent Gring
*Attorney, Agent, or Firm*—Garvey, Smith, Nehrbass & Doody, LLC

[57] ABSTRACT

A dual chamber syringe for dispensing a dry medicine that is to be reconstituted just prior to administration to a patient includes a syringe housing having an outer wall and proximal and distal end portions. A syringe bore extends between the proximal and distal end portions. The bore is divided during use into upper and lower chambers for containing medicinal contents that are to be first mixed and then dispensed. In the preferred embodiment, the chambers contain an upper liquid component and a lower dry component. A first lower piston occupies a position generally in between the upper and lower chambers. The first lower piston engages a plurality of ribs at an enlarged diameter bypass portal section of the syringe housing with multiple longitudinally extending channels after the user applies pressure to a second upper piston in the bore and above the upper chamber. Continued downward movement of the two pistons causes the two components to mix to be dispensed from the distal end of the syringe. The ribs have recess portions that form a dampening slot for engaging the periphery of the first lower piston as it travels distally. This enables the diluent fluid to completely mix with the dry drug product before the second, upper piston engages the lower piston to force it down during administration of the reconstituted product to the patient.

20 Claims, 4 Drawing Sheets

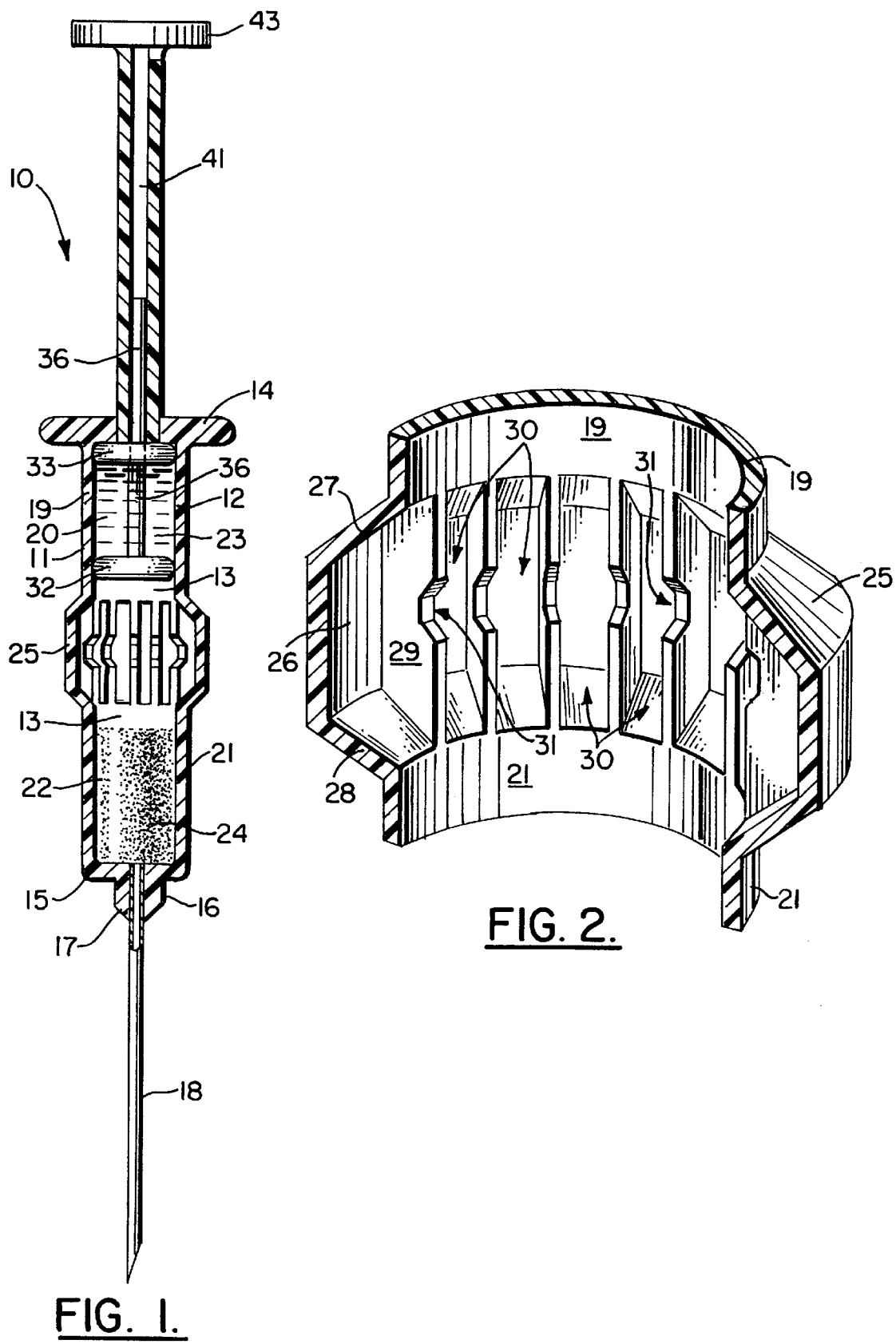

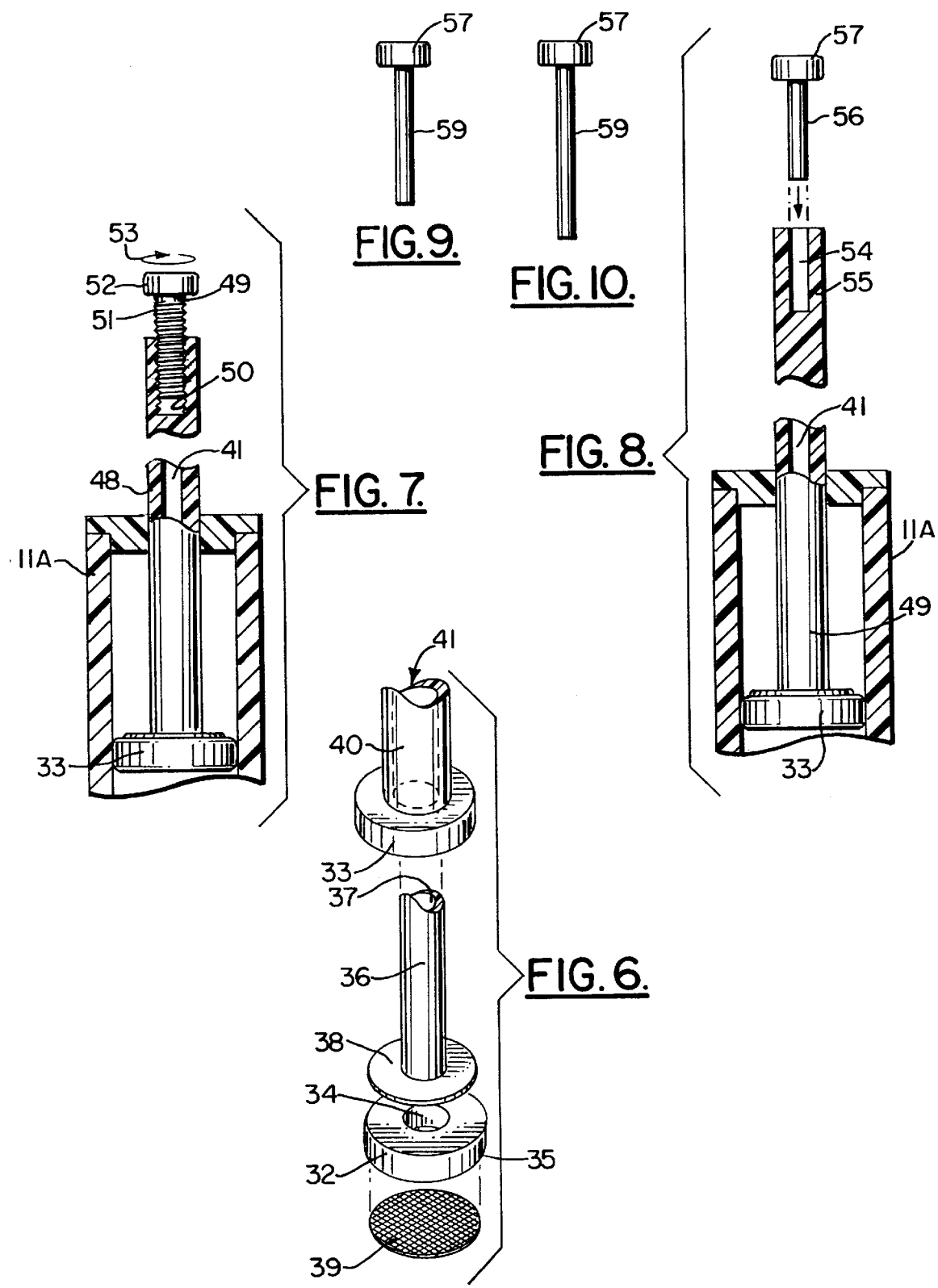

DUAL CHAMBER SYRINGE APPARATUS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A "MICROFICHE APPENDIX"

Not applicable.

BACKGROUND OF THE INVENTION

1. Field of the Invention

The present invention relates to syringes (manual, automatic and/or cartridge type), and more particularly to a double chambered syringe having a pair of pistons including an upper piston that is operable by the user and another piston that "floats" in between the upper piston and the distal, dispensing end of the syringe. Even more particularly, the present invention relates to a dual chamber syringe that has a pair of chambers positioned respectively in between the first and second pistons and in between the first "floating piston" and the distal, dispensing end of the syringe and wherein a plurality of longitudinally extending channels are provided at a middle portion of the syringe barrel so that when the first floating piston is positioned adjacent to the channels, liquid contained in the upper chamber can flow around the first piston and through the channels to the second chamber wherein a dry medicine is contained. A mixing of the liquid and dry medicine takes place in the second chamber. Continued downward movement of the two pistons dispenses the combined liquid and dry components (to an I.V. line, intermediary bottle, patient, etc.). The closure can be a closure cap, a Luer lock, or a needle/condom. For these dispensing and closure arrangements, a user simply inverts the syringe during dispensing.

2. General Background of the Invention

It is known that many drugs cannot be administered by the oral route because of gastrointestinal intolerance, irregularity in absorption, and metabolic breakdown in the gut wall and liver (first pass effects). In particular, first pass loss abolishes oral bioavailability of all polypeptide and protein medications [e.g. sermorelin acetate, follitropin beta growth hormone, insulin, glucagon, alteplase, erythropoietin, alglucerase (glucocerebrosidase-B-glucosidase), etc.]. This necessitates their administration through various parenteral routes, i.e., intravenous, intramuscular, subcutaneous, intrathecal, etc. Further, parenteral delivery of such drugs will expand with future mapping and functional understanding of the human genome. Pharmaceutical recombinant DNA synthesis of new peptide-protein moieties will concomitantly increase [e.g. megakaryocyte growth and development factor, tumor necrosis binding receptor, angiogenic growth factor, stem cell factor, neurotrophin-3, leptin, glial cell line-derived neurotrophic factor, nerve growth factor, etc.], and make a cost-contained, safe, effective and simple to use delivery device essential for both patients and medical professionals.

Functionally, stability of an injectable drug may be defined as its capability to retain chemical, sterile, toxicological and therapeutic specifications within 90% of its original potency. By tradition, expiration dates denote the last day of a month and year a particular preparation retains such stability under recommended conditions. In case of a dry or lyophilized medication to be reconstituted prior to use, expiration dates are designated for both the dry and reconstituted product. When compared to drug solutions ready for injection, dry soluble medications ready to be reconstituted with solvent just prior to use are well known to have greater stability and longer expiration dates.

Time related deterioration in ready to use parenteral drug preparations include interactions between combined active, and between active and inactive ingredients. Aqueous solvents in particular, potentiated by heat and radiation, initiate or accelerate time dependent drug degradation through oxidation, reduction, hydrolysis, racemization, decarboxylation, photolysis, and, autooxidative free radical chain reactions.

Notwithstanding such chemical breakdown, buffers, antioxidants, preservatives and other stabilizers oftentimes cannot be used in formulations containing water because of their reactivity with the active ingredient(s) or, direct patient hypersensitivity. Moreover, water itself has a profound effect on hydrolysis and denaturation of drugs possessing ester or amide chemical bonds, e.g. tetracaine, physostigmine, anagrelide, growth hormone, benzylpenicillin, calcitonin, epoetin alfa, menotropins, placental gonadotropin, interferons, pituitary releasing hormones (gonadorelin, cosyntropin, etc.) and numerous others.

A cost effective, simple, self contained dual-chamber syringe which isolates dry-wet drug components and mixes them immediately prior to injection is highly desirable. Furthermore, such a device would eliminate extra standard syringes, medication and diluent containers required for mixing the individual drug constituents. The device would permit accurate drug reconstitution, reduce time required for drug preparation, eliminate waste and possible introduction of contaminants through human error.

Various types of two compartment injection syringes have been patented to address such concerns and are known. U.S. Pat. No. 5,395,326 describes a medication jell-liquid two compartment syringe fitted with side-by-side chambers for mixing and injecting via a dilating O-ring piston assembly; U.S. Pat. No. 4,983,164 utilizes a two chambered syringe barrel created by a non-movable, separating membrane which ruptures when displaced toward the plunger.

Other patents, U.S. Pat. Nos. 4,413,991, 4,202,314 and 4,214,584 either possess dual chambers interconnected with side openings through an injection needle, or two driving systems for mixing and injecting, or have concentric dual chambers which upon manual rotation, untighten and permit mixing with subsequent standard injection.

Dual chamber syringes are known for administering medicinal preparations wherein it is desired to isolate a first medicinal preparation from a second medicinal preparation until it is time to administer the combination of the two preparations to a patient.

An example of a device for administering such first and second medicinal preparations is seen in the Smirnov et al. U.S. Pat. No. 4,214,584. The Smirnov device is provided for administering medicinal preparations that includes an isolated capsule divided into a chamber for a first medicinal preparation and a chamber for a second medicinal preparation. Coaxially inside the isolated capsule and concentrically therewith is the piston which bounds the chamber for the first medicinal preparation. Made fast on the piston is an injection needle having a hole located at the base of the piston. Provision is made in the device for a mechanical actuator of the piston, which is a spring-opposed pushrod located inside the housing which also accommodates the retaining member for the spring-opposed pushrod. The chamber for the second medicinal preparation is arranged concentrically with the chamber for the first medicinal preparation so as to embrace the latter. The isolated capsule is mounted traversably inside the housing, while communication between both of the chambers is established upon a positive extension of the isolated capsule from the housing outwards.

Another Smirnov patent is U.S. Pat. No. 4,202,314 entitled "Device For Injection Of Medicinal Preparations". The device for injection of medicinal preparations, comprises a changeable isolated capsule, an injection needle, and a drive to move pistons, made in the form of a spring-loaded pusher located inside the housing which supports the changeable isolated capsule. The housing has a stopping member to arrest said spring-loaded pusher. Inside said isolated capsule, installed coaxially therewith and with each other are a main piston closed by a partition on the side facing the chamber holding the first medicinal preparation and an additional piston. The partition is movable. The injection needle is installed inside the isolated capsule, fixed on the additional piston, and it in use passes through said partition, and has an aperture in the zone of the partition on the side of the chamber holding the first medicinal preparation. The additional piston is located in the channel of the main piston and limits the chamber for the second medicinal preparation. The drive of the pistons has an additional spring-loaded pusher interacting with the additional piston and is located coaxially with the spring-loaded pusher. The housing of the drive of the pistons has an additional stopping member for the additional spring-loaded pusher.

The Kamstra U.S. Pat. No. 4,529,403, entitled "Automatic Injection Syringe", relates to a syringe for injecting two or more different injection liquids which may not be contact with each other for long periods of time. For that purpose, the ampoule between the piston and the needle connection includes one or more stoppers which keep the injection liquids separated from each other, while at a point a short distance before the needle connection a by-pass means is present through which the injection liquid or injection liquids present behind the stopper or stoppers can pass the stopper or stoppers during use of the syringe.

In the Hook U.S. Pat. No. 4,983,164, an automatic two-chamber injector for mixing and injecting a medicinal solution is disclosed. The injector comprises a barrel having a first end with a receiving portion for an injection needle, that portion being sealed prior to use, and a second end with a displaceable plunger. The barrel comprises two chambers separated by a migration proof membrane, the membrane being adapted to rupture when the plunger is displaced towards the first end of the barrel. The '164 patent also discloses a method for mixing and injecting a solution by means of an automatic two-chamber injector and to a cartridge for a two-chamber injector.

European Patent Application No. 0 072 057 relates to an automatic syringe for injecting two or more different injection liquids which may not be in contact with each other for longer periods of time. For that purpose the ampoule between piston and needle connection comprises one or more stoppers which keep the injection liquids separated from each other, while at a short distance before the needle connection a by-pass means is present past which the injection liquid or injection liquids present behind the stopper or stoppers can pass the stopper or stoppers during use of the syringe.

One of the problems with dual chamber syringes is that of achieving a complete mixture of the medicinal components while at the same time perfecting a complete and total dispensing of the combined medicinal portions into the patient after mixing has been completed.

The syringes disclosed in the above-discussed patents do not provide a plurality of ribs that define flow channels therebetween and dampening slots that hold the first, lower piston until the diluent has completely mixed with the dry drug.

Many of the above-discussed prior art patents are highly complex structures comprising multiple interlocking and telescoping portions, some requiring springs for operation. The present invention is an improvement over these prior art patents. Unlike prior art dual chamber syringes, the apparatus of the present invention has only two moving parts, each being a piston sliding within a single one piece syringe barrel. Yet the present invention effectively isolates first and second medicinal portions before use, perfects mixture immediately prior to administration, and contains the mixed medicinal components below a lower piston in the syringe barrel to ensure complete discharge of the mixed medicinal components during administration to the patient.

SUMMARY OF THE INVENTION

The purpose of the present invention is to provide an improved two-chambered syringe which isolates, stores, mixes and ejects reconstituted dry-wet pharmaceuticals or other parenteral drugs that are unstable or have short expiration dates when prepared in ready to use formulations. The invention is cost effective to manufacture as either a prefilled two chambered manual syringe, or as a reloadable cartridge for automatic injection devices, e.g., U.S. Pat. No. 5,267, 963, incorporated herein by reference.

The device is depicted as a syringe with two chambers created and separated by a dividing piston that includes upper and lower plungers. Distally, the upper or liquid chamber is sealed by the lower plunger. The lower or dry drug chamber can be separated from the diluent liquid by an internal hydrophobic membrane that allows air but not water to pass through it.

The present invention thus provides an improved dual chamber syringe apparatus for dispensing a dry or unstable medicine that is to be reconstituted just prior to administration to a patient. The apparatus includes a syringe housing that is generally cylindrically shaped, having an outer wall and proximal and distal end portions. A middle section of the syringe housing is of an enlarged diameter.

A bore extends between the proximal and distal end portions, the bore including upper and lower chamber sections for containing medicine contents to be dispensed including an upper liquid component and a lower dry medicinal component. A dispensing needle at the distal end of the housing can be provided for receiving the medicine contents of the lower chamber after mixing.

A pair of pistons are provided that are separately movable. A lower piston occupies the position in between the ends of the syringe barrel, and in between the upper and lower chambers. The lower piston is movable between upper and lower positions. An upper piston is positioned at the proximal end of the housing and slides within the bore during use.

The enlarged diameter middle portion of the barrel carries one or a plurality of longitudinally extending channels. These channels are positioned at the middle of the housing and form a connection between the upper and lower chambers. The floating chamber has a maximum sidewall dimension that is less than the length of the channel or channels. The channels can therefore convey fluid in between the proximal and distal ends of the syringe and in between the upper and lower chambers when the first piston occupies a position adjacent the longitudinal channels and the ends of each channel extend beyond the ends of the lower piston.

The lower piston forms a seal to retain the liquid contents of the upper chamber away from the lower chamber when the first piston is in the upper position. The lower piston forms a seal that seals the combined liquid and dry contents from the channels prior to dispensing and after the liquid and dry medicinal portions have been reconstituted.

In the preferred embodiment, a hydrophobic membrane can be provided below in the lower chamber at the lower piston.

In accordance with the present invention, the dual chambered syringe contains longitudinally extending bypass channels. These longitudinal channels are part of an enlarged diameter section of the syringe barrel wall, so designed in depth and width as to facilitate thorough mixing of all pharmaceuticals.

The advantage is obtained by the mixing channels being critically placed to begin and end generally equi-distant from each end of the syringe so as to permit the lower chamber to accept and instantly retain a predetermined volume of diluent contained and transferred through the bypass channels from the upper chamber.

The dampening slot slows movement of the lower plunger so as to permit complete mixing of the diluent from the upper chamber with the dry medication in the lower chamber. The floating piston is forced from the dampening slot by the abutment of the upper piston against the lower piston. This occurs when all of the diluent fluid between the upper and lower plunger has passed through the ribbed by-pass portals into the lower chamber.

The length of the bypass portals is of any length greater than the length of the dividing piston but, no of such length as to encroach into the distal chamber of the syringe designed to contain a specified volume of diluent, or of such length as prevent the putative lower chamber from receiving the required volume for exact reconstitution and tight resealing by the dividing piston.

Operationally, downward force upon the upper plunger pressurizes the liquid in the upper chamber causing the lower plunger to move downward and enter the by-pass mixing portals. The bypass portals, now opened and confluent to each side of the lower plunger, cause accelerated fluid flow from the upper chamber to mix and reconstitute the dry contents in the lower drug chamber.

The present invention thus provides an improved, double chambered syringe apparatus that includes upper and lower plungers, each contained within a common bore of the one piece syringe barrel.

The barrel is comprised of three sections including an upper chamber section, a lower chamber section, and a middle enlarged diameter bypass portal section that contains one or more channels for transferring liquid contained in the upper chamber section to the lower chamber section.

The upper chamber section contains a prefilled diluent or stable liquid medication. The lower chamber contains a dry or lyophilized unstable medication. A lower piston seals and separates the liquid in the first chamber section away from the dry medication prior to use.

Pressure upon the upper piston pushes the liquid in the upper chamber downwardly. This downward pressure applied to the upper plunger also forces the lower plunger (a floating or dividing plunger) below to the middle or channeled portion of the syringe.

The liquid can then discharge from the upper chamber section and circumferentially enter by-pass channels, flowing around the lower piston to the lower chamber. This results in a reconstituting of the contained dry medication in the lower chamber section.

Further pressure will abut the upper piston against the movable lower piston, positioned in the dampening slot, eventually dispensing the now mixed or reconstituted wet/dry components as a parenteral injection.

The apparatus of the present invention will permit pre-filling of unstable drugs and medications such as prostaglandin $E_1$, erythropoietin, growth hormone, myeloid growth factors (Filgrastim®), Neumaga®, Ceredase®, glucagon, alteplase, alglucerase, interferons, thyrotropin, chorionic gonadotropin, menotropins, gonadorelin, sermorelin, urofollitropin, and other recombinant peptides/proteins and drugs that must be kept in dry or lyophilized form until time of use. Such aqueously unstable drugs can thus be kept in their dry form, separated from the diluent or other liquid medication of the upper chamber section until time of use in a dry-wet syringe, with or without attached needle. The dry chamber portion of the device can be vacuum or inert gas sealed should air or oxygen need to be eliminated.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 1 is a sectional elevational view of the preferred embodiment of the apparatus of the present invention;

FIG. 2 is a fragmentary perspective view of the preferred embodiment of the apparatus of the present invention;

FIG. 6 is partial perspective view of the preferred embodiment of the apparatus of the present invention;

FIG. 7 is a partial sectional elevational view of the preferred embodiment of the apparatus of the present invention showing an optional adjustable dosage plunger;

FIG. 8 is a partial sectional elevational view of the preferred embodiment of the apparatus of the present invention showing another dosage adjustment optional arrangement;

FIGS. 9 and 10 show partial perspective views of the dosage adjustment pins for use with the dosage adjustment configuration of FIG. 8.

DETAILED DESCRIPTION OF THE PREFERRED EMBODIMENT

Figure 3:
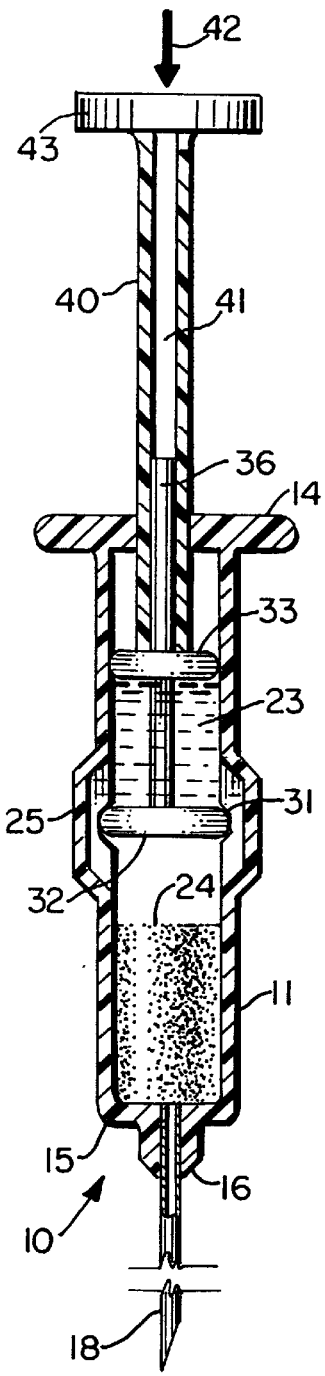
FIG. 3 is a sectional elevational view of the preferred embodiment of the apparatus of the present invention showing the lower piston end of the dampening slot at the initiation of mixing.

Dual chamber syringe apparatus 10 is shown generally in FIGS. 1 and 3–5. Syringe apparatus 10 includes a barrel 11 having a wall 12 and a central longitudinal bore 13. The barrel 11 has a proximal end 14 having a pair of opposed flanges as with conventional syringes and a distal end 15. Distal end 15 can be provided with an outlet fitting 16 having a dispensing opening 17 that communicates with needle 18 so that liquid contained within the syringe bore 13 can be discharged via the needle 18.

Syring barrel 11 includes an upper cylindrical section 19 having an upper chamber 20 for containing fluid and a lower cylindrical section 21 with a lower chamber 22. The upper chamber 20 contains a liquid diluent 23. Lower chamber 22 contains a dry medicine or drug 24.

An enlarged diameter section 25 is provided to syringe barrel 11 in between the proximal 14 and distal 15 ends. Enlarged diameter section 25 is shown more particularly in FIG. 2. The enlarged diameter section 25 includes a cylindrical wall 26, a frustoconical wall 27, a second frustoconical wall 28, and a plurality of radially and longitudinally extending ribs 29.

The ribs 29 have cutouts or recesses 31 that define in combination a dampening slot for receiving the periphery of lower piston 32. Each pair of ribs 29 defines therebetween a bypass flow channel 30. During use, the lower piston 32 registers in the dampening slot defined by recesses 31 so that the lower piston 32 is held by the recesses 31 until the liquid diluent 23 can flow via channels 30 from upper chamber 20 into lower chamber 22. There, it mixes with the dry drug 24.

In FIG. 1, upper piston 33 is positioned within the bore 13 of barrel 11 next to the proximal 14 end of barrel 11. The lower piston 32 is positioned in between enlarged diameter section 25 and distal end 14 of barrel 11. In this fashion, the upper chamber 20 is formed in between lower piston 32 and upper piston 33. The lower chamber 22 is that portion of syringe bore 13 below lower piston 32 or in between lower piston 32 and distal end 15 of syringe barrel 11 as shown in FIG. 1. In FIG. 1, the liquid diluent 23 contained in upper chamber 20 is separated from and sealed from the dry drug 24 in lower chamber 22.

Plunger 40 is used to move the upper piston 33 and lower piston 32 from the proximal end 14 of barrel 11 toward the distal 15 end portion thereof. This is shown in sequence in FIGS. 1 and 3–5.

In FIG. 1, the lower piston 32 is in its uppermost position as is the upper piston 33. In FIG. 3, pressure has been applied by a user to the proximal plunger head 43 of plunger 40 so that the plunger 40 moves in the direction of arrow 42. This causes the lower piston 32 to move downwardly until the periphery 35 of lower piston 32 engages the correspondingly shaped recesses 31 of ribs 29 forming the dampening slot.

In FIG. 3, lower piston 32 has registered in the plurality of recesses 31 of ribs 29 which define a dampening slot to prevent further downward movement of the lower piston 32. In FIG. 6, the lower piston 32 is shown having a central opening 35 that aligns with the bore or opening 37 through tubular member 36. The tubular member 36 has a disk 38 attached to its lower end portion as shown in FIG. 6.

The disk 38 registers against lower piston 32 while the opening 37 aligns with the opening 34. The tubular member 36 telescopes within bore 41 of plunger 40. A membrane 39 is affixed to the distal side of lower piston 32 opposite tubular member 36 and disk 38.

Figure 4:
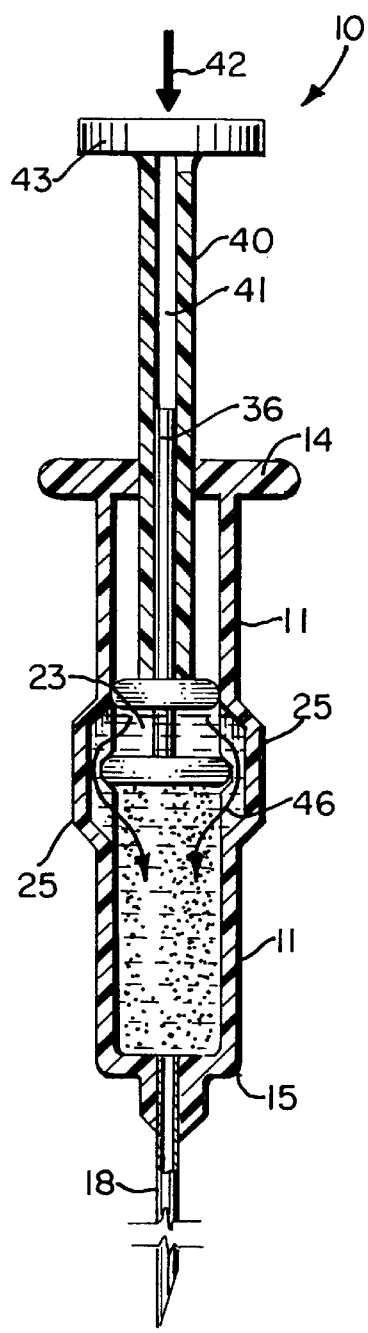
FIG. 4 is a sectional elevational view of the preferred embodiment of the apparatus of the present invention showing a mixing of the liquid diluent and dry medication.

Plunger 42 moves downwardly mixing the liquid diluent 23 with the dry drug 24 as shown in FIGS. 3–4. When the upper piston 33 engages the lower piston 32, continued downward movement of plunger 40 in the direction of arrow 42 causes both pistons 32, 33 to move downwardly so that the reconstituted drug product can be dispensed via needle 18 into the patient.

Figure 5:
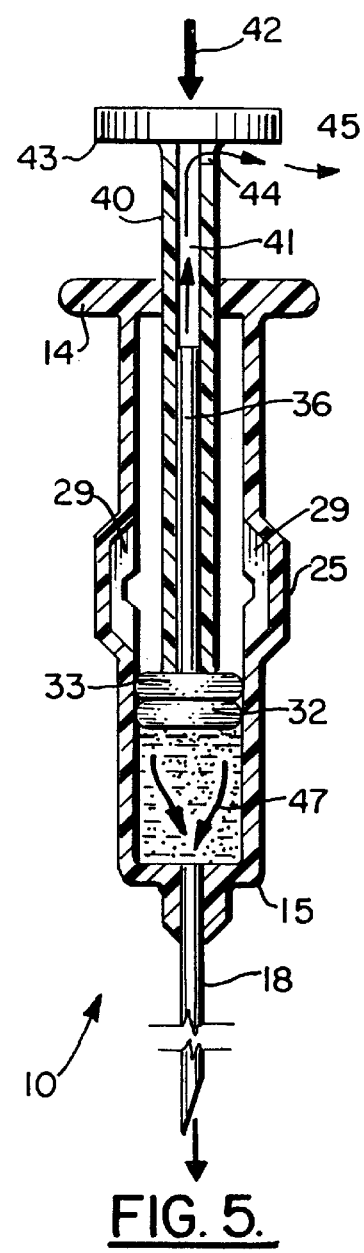
FIG. 5 is a sectional elevational view of the preferred embodiment of the apparatus of the present invention showing an administration of the reconstituted drug product.

As the two pistons 32, 33 move together, the tubular member 36 moves upwardly and is received into plunger bore 41. Any air contained in the lower chamber 22 can escape through membrane 39, opening 34 and opening 37 of tubular member 36 into plunger bore 41. Vent opening 44 at the proximal plunger head 43 of plunger 40 allows air to escape through opening 44 into the surrounding atmosphere as shown by the arrow 45 in FIG. 5. Arrow 46 in FIG. 4 illustrate the flow of diluent 23 from the upper chamber 20 to the lower chamber 22. Arrows 47 in FIG. 5 illustrate the administration of the reconstituted product from the lower chamber 22 into the patient via needle 18.

FIGS. 7–10 and 11–15 show a mechanism to adjust the dosage for the reconstituted drug product to be administered to a patient. In FIG. 7, plunger 48 cooperates with syringe barrel 11A having an upper piston 33. Otherwise, the lower piston 32 would be configured as with respect to the embodiment of FIGS. 1–6. The enlarged diameter section 25 would also be provided in syringe 11A as would be the portion of syringe barrel 11 below enlarged section 25 as seen in FIGS. 1 and 3–5. The plunger 48 has a hollow bore 41 that accepts tubular member 36. At its proximal end, plunger 48 has internal threads 50 that accept the external threads 51 of pin 49.

Pin 49 provides an adjustment knob 52 that can be rotated in either rotational direction as indicated by the arrow 53 in FIG. 7. By rotating the adjustment knob 52, plunger 48 can be lengthened or shortened to vary dosage. In FIGS. 8–9, plunger 48 has a socket 54 that receives one of a plurality of selected adjustment pins 56, 58, 59 of different length. Each pin 56, 58, 59 has an enlarged head 57. For each of the adjustment mechanisms of FIGS. 6–10, the syringe 10 would be placed as a cartridge in an automatic injection device as shown for example, in U.S. Pat. No. 5,267,963, incorporated herein by reference.

Figure 15:
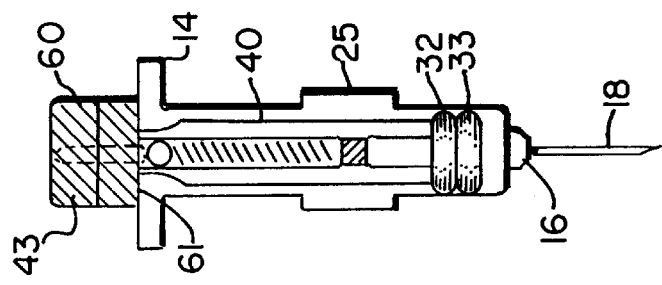
FIGS. 11–15 are elevational views of another dosage adjustment mechanism for use with the preferred embodiment of the apparatus of the present invention.
Figure 14:
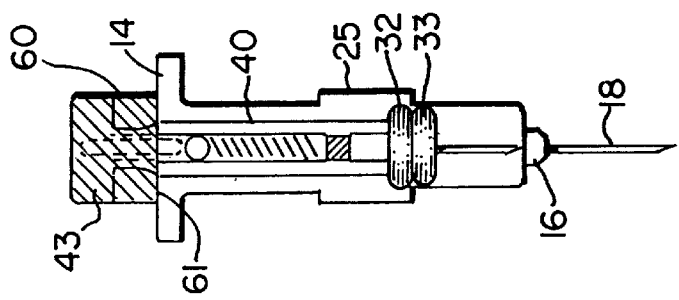
Figure 13:
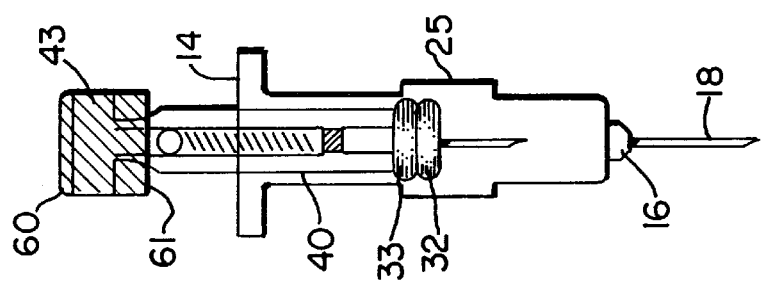
Figure 12:
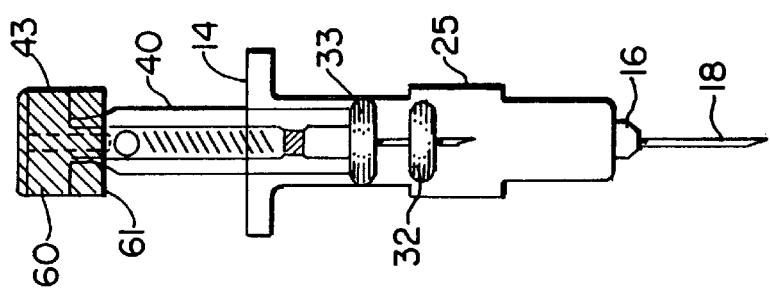
Figure 11:
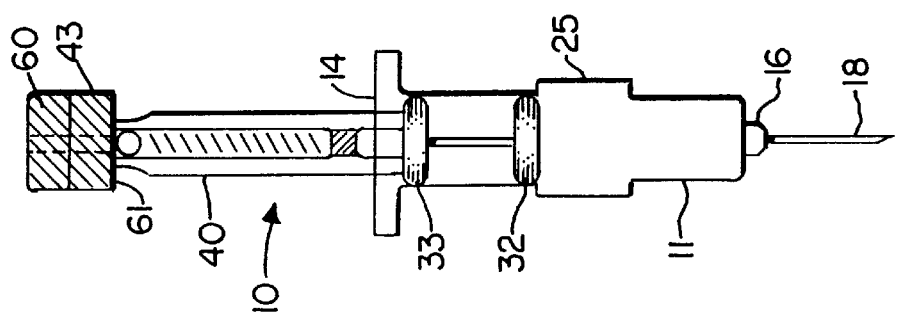

In FIGS. 11–15, a cap 60 is attachable to plunger head 43 using a threaded connection, for example. The distal surface 61 of cap 60 engages proximal end 14 of barrel 11 as shown in FIGS. 5 and 6 when the reconstituted drug product has been fully dispensed. In FIGS. 11 and 15, the cap 60 has been adjusted to provide a maximum dose while in FIGS. 12–14, the cap 60 has been adjusted to provide a minimal dose.

The following table lists the parts numbers and parts descriptions as used herein and in the drawings attached hereto.

| PARTS LIST | |
| --- | --- |
| Part Number | Description |
| 10 | syringe apparatus |
| 11 | barrel |
| 11A | barrel |
| 12 | wall |
| 13 | syringe bore |
| 14 | proximal end |
| 15 | distal end |
| 16 | outlet fitting |
| 17 | dispensing opening |
| 18 | needle |
| 19 | upper cylindrical section |
| 20 | upper chamber |
| 21 | lower cylindrical section |

-continued

PARTS LIST

| Part Number | Description |
| --- | --- |
| 22 | lower chamber |
| 23 | liquid diluent |
| 24 | dry drug |
| 25 | enlarged diameter section |
| 26 | cylindrical wall |
| 27 | frustoconical wall |
| 28 | frustoconical wall |
| 29 | rib |
| 30 | channel |
| 31 | recess |
| 32 | lower piston |
| 33 | upper piston |
| 34 | central opening |
| 35 | periphery |
| 36 | tubular member |
| 37 | opening |
| 38 | disk |
| 39 | membrane |
| 40 | plunger |
| 41 | plunger bore |
| 42 | arrow |
| 43 | proximal plunger head |
| 44 | vent opening |
| 45 | arrow |
| 46 | arrow |
| 47 | arrow |
| 48 | plunger |
| 49 | pin |
| 50 | internal threads |
| 51 | external threads |
| 52 | knob |
| 53 | arrow |
| 54 | socket |
| 55 | closed end |
| 56 | pin |
| 57 | enlarged head |
| 58 | pin |
| 59 | pin |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A dual chamber syringe for dispensing a dry medicine that is to be reconstituted just prior to administration to a patient comprising:
   a) a syringe housing having an outer wall and proximal and distal end portions;
   b) a bore that extends between the proximal and distal end portions, the bore including upper and lower chambers for containing medicine contents to be dispensed including an upper liquid component and a lower dry component;
   c) a dispensing portion at the distal end of the housing for receiving the medicine contents of the bore;
   d) a first piston that occupies a position generally in between the upper chamber and the lower chamber, the first piston being movable within the bore between upper and lower positions during use;
   e) a second piston positioned at the proximal end of the housing and movable within the bore between upper and lower positions during use;
   f) an enlarged diameter section of the housing defining a bypass bore section for enabling fluid travel between the upper and lower chambers;
   g) a plurality of bypass channels positioned in the bypass bore separated by a plurality of ribs, the ribs having recessed portions for receiving the periphery of the first piston as fluid flows through the longitudinal channels; and
   h) wherein the first piston seals the contents of the upper chamber away from the channels and lower chamber in the upper position.

2. The dual chamber syringe of claim 1 wherein the enlarged diameter section includes a cylindrically-shaped portion.

3. The dual chamber syringe of claim 1 wherein the enlarged diameter section of the housing has an external wall with inner and outer surfaces and the bypass channels are formed on the inner surface of the wall.

4. The dual chamber syringe of claim 1 wherein the bore is of a generally uniform diameter over a majority of the length of the syringe housing.

5. A dual chamber syringe for dispensing a dry medicine that is to be reconstituted just prior to administration to a patient comprising:
   a) a syringe housing having an outer wall and proximal and distal end portions;
   b) a bore that extends between the proximal and distal end portions, the bore including upper and lower chambers for containing medicine contents to be dispensed including an upper liquid component and a lower dry component;
   c) a dispensing portion at the distal end of the housing for receiving the medicine contents of the bore;
   d) a first piston that occupies a position generally in between the upper chamber and the lower chamber, the first piston being movable within the bore between upper and lower positions during use;
   e) a second piston positioned at the proximal end of the housing and movable within the bore between upper and lower positions during use;
   f) an enlarged diameter section of the housing defining bypass bore section for enabling fluid travel between the upper and lower chambers;
   g) a plurality of bypass channels positioned in the bypass bore separated by a plurality of ribs, the ribs having dampening slots for holding the first piston as fluid flows through the longitudinal channels;
   h) wherein the first piston seals the contents of the upper chamber away from the channels and lower chamber in the upper position; and
   i) a semi-permeable membrane positioned at the first piston for enabling air flow but not water flow through the first piston.

6. The dual chamber syringe of claim 5 wherein the first piston is a transverse member that extends across the bore forming an engagement with the external wall.

7. The dual chamber syringe of claim 6 wherein the first piston has an opening therethrough.

8. The dual chamber syringe of claim 1 wherein the first piston has an O-ring like seal that forms a seal between the first piston and the housing when the first piston is in the upper position.

9. A dual chamber syringe for dispensing a dry medicine that is to be reconstituted just prior to administration to a patient comprising:
   a) a syringe housing having an outer wall and proximal and distal end portions;
   b) a bore that extends between the proximal and distal end portions, the bore including upper and lower chambers for containing medicine contents to be dispensed including an upper liquid component and a lower dry component;

c) a dispensing portion at the distal end of the housing for receiving the medicine contents of the bore;

d) a first piston that occupies a position generally in between the upper chamber and the lower chamber, the first piston being movable within the bore between upper and lower positions during use;

e) a second piston positioned at the proximal end of the housing and movable within the bore between upper and lower positions during use;

f) an enlarged diameter section of the housing defining bypass bore section for enabling fluid travel between the upper and lower chambers;

g) a plurality of bypass channels positioned in the bypass bore separated by a plurality of ribs, the ribs having dampening slots for holding the first piston as fluid flows through the longitudinal channels; and h) wherein the first piston seals the contents of the upper chamber away from the channels and lower chamber in the upper position;

i) wherein the first piston has a central opening and a hollow tube connected to the piston at the opening so that air can flow through the central opening and tube and further comprising a membrane that allows air but not water to flow through the opening and hollow tube.

10. The dual chamber syringe of claim 9 wherein a plurality of the longitudinal channels are generally parallel.

11. A dual chamber syringe, comprising:

a) a syringe housing having an outer wall and proximal and distal end portions;

b) a syringe bore that extends between the proximal and distal end portions, the bore defining upper and lower chambers for containing medicinal contents to be dispensed including an upper liquid component and a lower dry component;

c) a dry medicine contained within the lower chamber;

d) a liquid diluent contained within the upper chamber for reconstituting the dry medicine just prior to administration to a patient;

e) a dispensing needle at the distal end of the housing for receiving the medicinal contents of the bore after the liquid is used to liquify the dry medicine;

f) a first, lower piston that occupies a position generally in between the upper chamber and the lower chamber, the first piston having a central opening and being movable between upper and lower positions;

g) a second, upper piston positioned at the proximal end of the housing and sliding in the bore during use, and the first piston being movable relative to the second piston;

h) a hollow plunger for urging the second upper piston downwardly toward the distal end of the housing, the plunger having a central opening;

i) at least one longitudinal channel positioned at the center of the housing that conveys liquid in between the upper and lower chambers when the first piston moves from the upper to the lower position;

j) wherein the first piston seals the liquid contents of the upper chamber away from the dry contents of the lower chamber when the first position is in the upper position;

k) wherein the first position is positioned next to the channel when the first piston is moving from the upper position to the lower position; and l) a hollow tube connected to the first, lower piston at the central opening, the tube being telescopingly received within the plunger central opening; and m) a semi-permeable, hydrophobic membrane that enables air but not water to flow through the central opening of the first piston into the hollow tube and central opening of the plunger; and n) a vent opening for venting air from the hollow tube and central opening of the plunger.

12. The dual chamber syringe of claim 11 wherein the membrane is positioned on the first piston in communication with the lower chamber.

13. The dual chamber syringe of claim 11 wherein there are a plurality of channels.

14. The dual chamber syringe of claim 11 wherein the channel comprises an enlarged diameter section of the syringe bore.

15. The dual chamber syringe of claim 14 wherein the enlarged diameter section of the syringe bore includes a plurality of longitudinally extending ribs.

16. The dual chamber syringe of claim 15 wherein the ribs have recessed portions forming a dampening slot that slows downward movement of the first piston during use.

17. The dual chamber syringe of claim 15 wherein each rib has a generally semicircular recess that receives a correspondingly shaped surface on the periphery of the first piston.

18. The dual chamber syringe of claim 11 wherein the membrane is of an oleophobic mesh material.

19. The dual chamber syringe of claim 11 wherein the plunger has an air outlet opening that enables air to flow from the plunger central opening to the surrounding atmosphere.

20. A dual chamber syringe, comprising:

a) a syringe housing having an outer wall and proximal and distal end portions;

b) a syringe bore that extends between the proximal and distal end portions, the bore defining upper and lower chambers for containing medicinal contents to be dispensed including an upper liquid component and a lower dry component;

c) a dry medicine contained within the lower chamber;

d) a liquid diluent contained within the upper chamber for reconstituting the dry medicine just prior to administration to a patient;

e) a dispensing needle at the distal end portion of the housing for receiving the medicinal contents of the bore after the liquid is used to liquify the dry medicine;

f) a first, lower piston that occupies a position generally in between the upper chamber and the lower chamber, the first piston having a central opening and being movable between upper and lower positions;

g) a second, upper piston positioned at the proximal end of the housing and sliding in the bore during use, and the first piston being movable relative to the second piston;

h) a hollow plunger for urging the second upper piston downwardly toward the distal end of the housing, the plunger having a central opening;

i) an enlarged diameter bypass portal section of the syringe housing positioned in between proximal and distal ends of the syringe housing having an enlarged diameter section of the syringe bore that provides a bypass channel for enabling diluent fluid to flow from the upper to the lower chamber, the enlarged diameter bypass portal section including means for supporting the periphery of the first, lower piston as the lower piston travels toward the lower chamber;

j) wherein the first piston seals the liquid contents of the upper chamber away from the dry contents of the lower chamber when the first piston is in the upper position;

k) wherein the first piston is positioned next to the channel when the first piston is moving from the upper position to the lower position; and l) a hollow tube connected to the first, lower piston at the central opening, the tube being telescopingly received within the plunger central opening; and m) a membrane that enables water but not air to flow through the central opening of the first piston into the hollow tube and central opening of the plunger; and n) a vent opening for venting air from the hollow tube and central opening of the plunger.

* * * * *